United States Patent [19]
Martin et al.

[11] Patent Number: 5,097,094
[45] Date of Patent: Mar. 17, 1992

[54] INBRED CORN LINE PHP60

[75] Inventors: Philip R. Martin, Alburnett; Robert R. Fincher, Des Moines, both of Iowa; James A. Wright, Union City, Tenn.

[73] Assignee: Pioneer Hi-Bred International, Inc., Des Moines, Iowa

[21] Appl. No.: 402,011

[22] Filed: Aug. 30, 1989

[51] Int. Cl.$^5$ .................. A01H 5/00; A01H 4/00; C12N 5/04
[52] U.S. Cl. ................... 800/200; 800/250; 800/DIG. 56; 435/240.4; 435/240.49; 435/240.5
[58] Field of Search ............ 800/200, 250, DIG. 56; 47/58, DIG. 1

[56] References Cited

U.S. PATENT DOCUMENTS 4,812,600  3/1989  Jensen et al. .................... 800/1

OTHER PUBLICATIONS

Nowacki et al. (1972), Bull de l'Academ Polonaise des Science 20(10): pp. 695–698.
Bates et al. (1974), Dept. Grain Sci. Kans. Landres Mexico, CIMNYT. (Abs. relied on).
Sprague et al. (1977), In/*Corn & Corn Improvement* Ed. Sprague et al., ASA, Madison, Wis., p. 316.
Galinat (1977), In/Corn & Corn Improvement Ed. Sprague et al. ASA, Madison, Wis., pp. 1 & 35.
Green et al. (1982) In/Maize for Biological Research, Ed. Sheridan, pp. 367–372, Ph. Mol. Biol. Assoc. U Press N. Dakota.
Germplasm Resources Information Network (1950), PI 184286, *Zea mays.*
Germplasm Information Network (1960), PI 262587, *Zea mays.*
Sass (1977), "Morphology" In/*Corn & Corn Improvement*, pp. 87–110, Amer. Soc. Agron. Publisher., Madison, Wis.
Conger, B. V. et al., "Somatic Embryogenesis from Cultured Leaf Segments of *Zea mays*", Plant Cell Reports 6:345–347 (1987).
Duncan et al., "The Production of Callus Capable of Plant Regeneration from Immature Embryos of Numerous *Zea mays* Genotypes", Planta (1985) 165:322–332.
Songstad et al., "Effect of ACC (1-Aminocyclopropane-1-Carboxylic Acid), Silver Nitrate, and Norbornadiene on Plant Regeneration from Maize Callus Cultures", Plant Cell Reports 7:262–265 (1988).
K. V. Rao et al., "Somatic Embryogenesis in Glume Callus Cultures", Maize Genetics Cooperation Newsletter (1986), vol. 60.

*Primary Examiner*—Elizabeth C. Weimar
*Assistant Examiner*—Gary Benzion
*Attorney, Agent, or Firm*—Michael J. Roth

[57] ABSTRACT

According to the invention, there is provided an inbred corn line, designated PHP60. This invention thus relates to the plants and seeds of inbred corn line PHP60 and to methods for producing a corn plant produced by crossing the inbred line PHP60 with itself or with another corn plant. This invention further relates to hybrid corn seeds and plants produced by crossing the inbred line PHP60 with another corn line or plant and to crosses with related species.

6 Claims, No Drawings 5,097,094

INBRED CORN LINE PHP60

FIELD OF THE INVENTION

This invention is in the field of corn breeding, specifically relating to an inbred corn line designated PHP60.

BACKGROUND OF THE INVENTION

The goal of plant breeding is to combine in a single variety/hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produce a uniform population of hybrid plants that may be heterozygous for many gene loci. A cross of two plants each heterozygous at a number of gene loci will produce a population of hybrid plants that differ genetically and will not be uniform.

Corn plants (Zea mays L.) can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbred lines are developed by selfing and selection of desired phenotypes. The new inbreds are crossed with other inbred lines and the hybrids from these crosses are evaluated to determine which of those have commercial potential.

Pedigree breeding for single-gene traits starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_5$, etc.

Backcrossing can be used to improve an inbred line. Backcrossing transfers a specific desirable trait from one inbred or source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for the desired trait to be transferred from the non-recurrent parent. After five or more backcross generations with selection for the desired trait, the progeny will be heterozygous for loci controlling the characteristic being transferred, but will be like the superior parent for most or almost all other genes. The last backcross generation would be selfed to give pure breeding progeny for the gene(s) being transferred.

A single cross hybrid corn variety is the cross of two inbred lines, each of which has a genotype which complements the genotype of the other. The hybrid progeny of the first generation is designated $F_1$. In the development of hybrids only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a hybrid corn variety involves three steps: (1) the selection of plants from various germplasm pools; (2) the selfing of the selected plants for several generations to produce a series of inbred lines, which, although different from each other, each breed true and are highly uniform; and (3) crossing the selected inbred lines with unrelated inbred lines to produce the hybrid progeny ($F_1$). During the inbreeding process in corn, the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid is produced from four inbred lines crossed in pairs ($A \times B$ and $C \times D$) and then the two $F_1$ hybrids are crossed again ($A \times B) \times (C \times D$). Much of the hybrid vigor exhibited by $F_1$ hybrids is lost in the next generation ($F_2$). Consequently, seed from hybrid varieties is not used for planting stock.

Corn is an important and valuable field crop. Thus, a continuing goal of plant breeders is to develop high-yielding corn hybrids that are agronomically sound based on stable inbred lines. The reasons for this goal are obvious: to maximize the amount of grain produced with the inputs used and minimize susceptibility to environmental stresses. To accomplish this goal, the corn breeder must select and develop superior inbred parental lines for producing hybrids. This requires identification and selection of genetically unique individuals which in a segregating population occur as the result of a combination of crossover events plus the independent assortment of specific combinations of alleles at many gene loci which results in specific genotypes. Based on the number of segregating genes, the frequency of occurrence of an individual with a specific genotype is less than 1 in 10,000. Thus, even if the entire genotype of the parents has been characterized and the desired genotype is known, only a few if any individuals having the desired genotype may be found in a large $F_2$ or $S_0$ population. Typically, however, the genotype of neither the parents nor the desired genotype is known in any detail.

SUMMARY OF THE INVENTION

According to the invention, there is provided a novel inbred corn line, designated PHP60. This invention thus relates to the seeds of inbred corn line PHP60, to the plants of inbred corn line PHP60, and to methods for producing a corn plant produced by crossing the inbred line PHP60 with itself or another corn line. This invention further relates to hybrid corn seeds and plants produced by crossing the inbred line PHP60 with another corn line or a related species.

DEFINITIONS

In the description and examples that follow, a number of terms are used herein. In order to provide a clear and consistent understanding of the specification and claims, including the scope to be given such terms, the following definitions are provided:

BAR PLT=BARREN PLANTS. This is the number of plants per plot that were not barren (lack ears).

BRT STK=BRITTLE STALKS. This is a measure of the stalk breakage near the time of pollination, and is an indication of whether a hybrid or inbred would snap or break near the time of flowering under severe winds. Data are presented as percentage of plants that did not snap.

BU ACR=YIELD (BUSHELS/ACRE). Actual yield of the grain at harvest adjusted to 15.5% moisture. ABS is in absolute terms and % MN is percent of the mean for the experiments in which the inbred or hybrid was grown.

CLD TST=COLD TEST. This is the percentage of kernels that germinate under cold soil conditions. ABS=absolute measurement and % MN is percentage of mean of the experiments in which inbred or hybrid was grown.

COB SC=COB SCORE. The cob score is a rating of how well the grain is shelled off the cob and how badly the cob is broken up going through the combine. This is given as a 1 to 9 score with 9 being very good. A high score indicates that the grain shells off of the cob well, and the cob does not break.

DRP EAR32 DROPPED EARS. This is a measure of the number of dropped ears per plot and represents the percentage of plants that did not drop ears prior to harvest.

EAR HT=EAR HEIGHT. The ear height is a measure from the ground to the top developed ear node attachment and is measured in inches.

EAR SZ=EAR SIZE. A 1 to 9 visual rating of ear size. The higher the rating the larger the ear size.

EST CNT=EARLY STAND COUNT. This is a measure of the stand establishment in the spring and represents the number of plants that emerge on a per plot basis for the inbred or hybrid.

GDU SHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86° F. and the lowest minimum temperature used is 50° F. For each inbred or hybrid it takes a certain number of GDUs to reach various stages of plant development.

GDU SLK=GDU TO SILK. The number of growing degree units required for an inbred line or hybrid to have approximately 50 percent of the plants with silk emergence from time of planting. Growing degree units are calculated by the Barger Method as given in GDU SHD definition.

GRN QUL=GRAIN QUALITY. This is a 1 to 9 rating for the general quality of the shelled grain as it is harvested based on such factors as the color of the harvested grain, any mold on the grain, and any cracked grain. High scores indicate good grain quality.

KER LB=KERNELS PER POUND. This is the number of kernels per 0.1 pound.

KSZ L=KERNEL SIZE LARGE. Percentage by weight of shelled corn that passes through a screen with 25/64 inch diameter openings but does not pass through a screen with 22/64 inch diameter openings.

KSZ MF=KERNEL SIZE MEDIUM FLAT. Percentage by weight of shelled corn that passes through a screen with 22/64 inch diameter openings and a screen with 13/64 inch wide slot screen but does not pass through a screen with 18.5/64 inch diameter openings.

KSZ MR=KERNEL SIZE MEDIUM ROUND. Percentage by weight of shelled corn that passes through a screen with 22/64 inch diameter openings but does not pass through a 13/64 inch wide slot screen or a screen with 18.5/64 inch diameter openings.

KSZ S=KERNEL SIZE SMALL. Percentage by weight of shelled corn that passes through a screen with 18.5/64 inch diameter openings but does not pass through a screen with 16/64 inch diameter openings.

KSZ TIP=KERNEL SIZE TIPS. Percentage by weight of shelled corn that passes through a screen with 16/64 inch diameter openings.

KSZ XL=KERNEL SIZE EXTRA LARGE. Percentage by weight of shelled corn that does not pass through a screen with 25/64 inch diameter openings.

MST=HARVEST MOISTURE. The moisture is the actual percentage moisture of the grain at harvest.

PLT HT=PLANT HEIGHT. This is a measure of the height of the plant from the ground to the tip of the tassel in inches.

POL WT=POLLEN WEIGHT. This is the weight of pollen per 100 plants taken on a plot basis. ABS refers to data in absolute, and % MN refers to data presented as percentage of experimental mean.

PRM=PREDICTED RM. This trait, predicted relative maturity (RM), is based on the harvest moisture of the grain. The relative maturity rating is based on a known set of checks and utilizes standard linear regression analyses and is referred to as the Minnesota Relative Maturity Rating System.

RT LDG=ROOT LODGING. Root lodging is the percentage of plants that do not root lodge; plants that lean from the vertical axis at an approximately 30° angle or greater would be counted as root lodged.

SCT GRN=SCATTER GRAIN. A 1 to 9 visual rating indicating the amount of scatter grain (lack of pollination or kernel abortion) on the ear. The higher the score the less scatter grain.

SDG VGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A corn breeder may utilize his or her own set of traits for the selection index. One of the traits that is almost always included is yield. The selection index data presented in the tables represent the mean value averaged across testing stations.

STA GRN=STAY GREEN. Stay green is the measure of plant health near the time of black layer formation (physiological maturity). A high score indicates better late-season plant health.

STK CNT=NUMBER OF PLANTS. This is the final stand or number of plants per plot.

STK LDG=STALK LODGING. This is the percentage of plants that did not stalk lodge (stalk breakage) as measured by either natural lodging or pushing the stalks and determining the percentage of plants that break below the ear.

TAS BLS=TASSEL BLAST. A 1 to 9 visual rating was used to measure the degree of blasting (necrosis due to heat stress) of the tassel at time of flowering. A 1 would indicate a very high level of blasting at time of flowering, while a 9 would have no tassel blasting.

TAS SZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEX EAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data is given as percentage of tillers: number of tillers per plot divided by number of plants per plot.

TST WT=TEST WEIGHT UNADJUSTED. The measure of the weight of the grain in pounds for a given volume (bushel).

TST WTA=TEST WEIGHT ADJUSTED. The measure of the weight of the grain in pounds for a given volume (bushel) adjusted for percent moisture.

YLD=YIELD. It is the same as BU ACR ABS.

YLD SC=YIELD SCORE. A 1 to 9 visual rating was used to give a relative rating for yield based on plot ear piles. The higher the rating the greater visual yield appearance.

CLN=Corn Lethal Necrosis (MCMV=Maize Chlorotic Mottle Virus and MDMV=Maize Dwarf Mosaic Virus): Visual rating (1-9 score) where a "1" is very susceptible and a "9" is very resistant.

MDM CPX=Maize Dwarf Mosaic Complex (MDMV=Maize Dwarf Mosaic Virus & MCDV=Maize Chlorotic Dwarf Virus): Visual rating (1-9 score) where a "1" is very susceptible and a "9" is very resistant.

COM SMT=Common Smut (*Ustilago maydis*): Percentage of plants that did not have infection.

ANT ROT=Anthracnose Stalk Rot (Colletotrichum graminicola): Visual rating (1-9 score) where a "1" is very susceptible and a "9" is very resistant.

SLF BLT=Southern Leaf Blight (*Bipolaris maydis*, *Helminthosporium maydis*): Visual rating (1-9 score) where a "1" is very susceptible and a "9" is very resistant.

NLF BLT=Northern Leaf Blight (*Exserohilum turcicum*, H. turcicum): Visual rating (1-9 score) where a "1" is very susceptible and a "9" is very resistant.

HC BLT=*Helminthosporium Carbonum* Leaf Blight (Bipolariszeicola, *H. carbonum*): Visual rating (1-9 score) where a "1" is very susceptible and a "9" is very resistant.

COM RST=Common Rust (*Puccinia sorghi*): Visual rating (1-9 score) where a "1" is very susceptible and a "9" is very resistant.

SO RST=Southern Rust (*Puccinia polysora*): Visual rating (1-9 score) where a "1" is very susceptible and a "9" is very resistant.

EYE SPT=Eyespot (*Kabatiella zeae*): Visual rating (1-9 score) where a "1" is very susceptible and a "9" is very resistant.

GLF SPT=Gray Leaf Spot (*Cercospora zeae-maydis*): Visual rating (1-9 score) where a "1" is very susceptible and a "9" is very resistant.

STW WLT=Stewart's Wilt (*Erwinia stewartii*): Visual rating (1-9 score) where a "1" is very susceptible and a "9" is very resistant.

GOS WLT=Goss's Wilt (*Corynebacterium nebraskense*): Visual rating (1-9 score) where a "1" is very susceptible and a "9" is very resistant.

HD SMT=Head Smut (*Spacelotheca reiliana*): Percentage of plants that did not have infection.

DNY MIL=Downy Mildew (*Peronosclerospora sorghi*): Percentage of plants that did not have infection.

FUS EAR=Fusarium Ear Mold (*Fusarium moniliforme*): Percentage of plants that did not have infection.

EAR MLD=General Ear Mold: Visual rating (1-9 score) where a "1" is very susceptible and a "9" is very resistant. This is based on overall rating for ear mold of mature ears without determining specific mold organism, and may not be predictive for a specific ear mold.

ECB DPE=Dropped ears due to European Corn Borer (*Ostrinia nubilalis*): Percentage of plants that did not drop ears under second brood corn borer infestation.

ECB 2SC=European Corn Borer Second Brood (*Ostrinia nubilalis*): Visual rating (1-9 score) of post flowering damage due to infestation by European Corn Borer. A "1" is very susceptible and a "9" is very resistant.

ECB 1LF=European Corn Borer First Brood (*Ostrinia nubilalis*): Visual rating (1-9 score) of pre-flowering leaf feeding by European Corn Borer. A "1" is very susceptible and a "9" is very resistant.

ECB 2IT=European Corn Borer Second Brood Tunneling (*Ostrinia nubilalis*): The average inches of tunneling in the stalk due to second brood (post-flowering) European Corn Borer infestation. Determined by splitting stalks with a knife, from four internodes above the ear to the ground.

DETAILED DESCRIPTION OF THE INVENTION

Inbred Corn Line PHP60 is a yellow, dent corn inbred with superior characteristics and provides an acceptable female parental line in crosses for producing first generation $F_1$ corn hybrids. This inbred is best adapted over the Southeastern areas of the United States. The inbreds can be used to produce hybrids from approximately 122-136 relative maturity based on the Minnesota Relative Maturity Rating System for harvest moisture of grain. PHP60 is best used as the female parent because of its acceptable female yields, but it is not acceptable as a male parent because of poor pollen shed. In the pollen yield test, PHP60 averaged only 51 percent (51%) of the experimental mean for amount of pollen in the pollen yield test averaged over 9 locations.

The inbred has shown uniformity and stability within the limits of environmental influence for all the traits as described in the Variety Description Information (Table 1) that follows. Most of the data in the Variety Description Information was collected at Johnston, Iowa. This inbred has been self-pollinated and ear-rowed a sufficient number of generations with careful attention paid to uniformity of plant type to ensure homozygosity and phenotypic stability. The line has been increased both by hand and in isolated fields with continued observations for uniformity. No variant traits have been observed or are expected in PHP60.

Inbred corn line PHP60, being substantially homozygous, can be reproduced by planting seeds of the line, growing the resulting corn plants under self-pollinating or sibpollinating conditions with adequate isolation, and harvesting the resulting seed, using techniques familiar to the agricultural arts.

TABLE 1
PHP60
VARIETY DESCRIPTION INFORMATION

A. Type: Dent      Region Best Adapted: Southeast
Maturity: Average across southern maturity zone Zone: 9
INBRED = PHP60
Heat Unit Shed: 1590
Heat Unit Silk: 1610
No. Reps: 32

$$\text{HEAT UNITS} = \frac{[\text{Max. Temp.} (<-86° F.) + \text{Min. Temp} (>-50° F.)]^*}{2} - 50$$

B. Plant Characteristics:
Plant height (to tassel tip): 246 cm
Length of top ear internode: 13 cm
Number of ears per stalk: single
Ear height (to base of top ear): 103 cm
Number of tillers: None
Cytoplasm type: Normal C. Leaf:
Color: (B14) Dark green
Angle from Stalk: <30 degrees
Marginal Waves: (OH7L) Many
Number of Leaves (mature plants): 22
Sheath Pubescence: (W22) Light
Longitudinal Creases: (OH56A) Few
Length (Ear node leaf): 84 cm
Width (widest point, ear node leaf): 9 cm D. Tassel:
Number lateral branches: 9
Branch Angle from central spike: <30 degrees
Pollen Shed: Light based on pollen Yield test (51% of experiment mean
Peduncle Length (top leaf to basal branches): 23 cm
Anther Color: Pinkish yellow
Glume Color: Green E. Ear (Husked Ear Data Except When Stated Otherwise):
Length: 17 cm
Weight: 84 cm
Mid-point Diameter: 37 mm
Silk Color: Greenish Yellow
Husk Extension (Harvest stage): Long (8-10 cm Beyond Ear tip)
Husk Leaf: Long (>15 cm)
Taper of Ear: Slight Taper
Position of Shank (dry husks): Upright
Kernel Rows: Straight, Distinct, Number = 14
Husk Color (fresh): Light green
Husk Color (dry): Buff
Shank Length: 17 cm

TABLE 1-continued
PHP60
VARIETY DESCRIPTION INFORMATION

Shank (No. of internodes): 10

F. Kernel (Dried):
Size (from ear mid-point)
Length: 9 mm
Width: 8 mm
Thick: 6 mm
Shape Grade (% rounds): 40-60% medium rounds base on Parent Test Data
Pericarp Color: Colorless
Aleurone Color: Homozygous Yellow
Endosperm Color: Yellow
Endosperm Type: Normal
Gm Wt/100 Seeds (unsized): 24 gm G. Cob:
Diameter at mid-point: 25 mm
Strength: Strong
Color: White H. Diseases:
Corn Lethal Necrosis (MCMV = Maize Chlorotic Mottle Virus and MDMV = Maize Dwarf Mosaic Virus): Susceptible
Maize Dwarf Mosaic Complex (MDMV & MCDV = Maize Chlorotic Dwarf Virus): Susceptible
Anthracnose Stalk Rot (*C. Graminicola*): Intermediate
S. Leaf Blight (*H. Maydis*): Intermediate
N. Leaf Blight (*H. Turcicum*): Intermediate
Carbonum Leaf Blight (*H. Carbonum*): Intermediate
Common Rust (*P. Sorghi*): Intermediate
Eye Spot (*K. Zeae*): Resistant
Gray Leaf Spot (*C. Zeae*): Intermediate
Stewarts Wilt (*E. Stewartii*): Intermediate
Common Smut (*U. Maydis*): Susceptible
Head Smut (*S. Reiliana*): Intermediate
Downy Mildew (*S. Sorghi*): Susceptible
Fusarium Ear Mold (*F. Moniliforme*): Intermediate I. Insects:
European Corn Borer-1 Leaf Damage (Pre-flowering): Suscepitible
European Corn Borer-2 (Post-flowering): Intermediate J. Variety Most Closely Resembling:
Character    Inbred
Maturity    PHN47
Usage    B73

*If maximum is greater than 86 degrees fahrenheit, then 86 is used and if minimum is less than 50, then 50 is used. Heat units accumulated daily and can not be less than 0.

PHN47 (PVP certificate 8800217) is a Pioneer Hi-Bred International, Inc. proprietary inbred. B73 is a public inbred released by Iowa State University that has been widely used.

Data for items B, C, D, E, F, & G are primarily based on 3 reps of data from Johnston, Iowa in 1987 and 1988 plus description information from the maintaining station.

TABLE 2
ELECTROPHORESIS RESULTS
Isozyme Genotypes for PHP60

Isozyme data was generated for inbred corn line PHP60 according to the procedure described in Goodman, M.M. and Stuber, C.M., "Genetic identification of lines and crosses using isoenzyme electrophoresis," Proceedings of the Thirty-Fifth Annual Corn and Sorghum Industry Research Conference, Chicago, Illinois (1980).

| | Alleles Present |
|---|---|
| Loci | PHP60 |
| ACP1 | 4 |
| ADH1 | 4 |
| CAT3 | 9 |
| DIA1 | 12 |
| GOT1 | 4 |
| GOT2 | 4 |
| GOT3 | 4 |
| IDH1 | 4 |

TABLE 2-continued

ELECTROPHORESIS RESULTS
Isozyme Genotypes for PHP60

| | |
|---|---|
| IDH2 | 6 |
| MDH1 | 6 |
| MDH2 | 6 |
| MDH3 | 16 |
| MDH4 | 12 |
| MDH5 | 12 |
| MMM | 4 |
| PGM1 | 9 |
| PGM2 | 4 |
| PGD1 | 2 |
| PGD2 | 5 |
| PHI1 | 4 |

INDUSTRIAL APPLICABILITY

This invention also is directed to methods for producing a corn plant by crossing a first parent corn plant with a second parent corn plant wherein the first or second parent corn plant is an inbred corn plant from the line PHP60. Further, both first and second parent corn plants can come from the inbred corn line PHP60. Thus, any such methods using the inbred corn line PHP60 are part of this invention: selfing, backcrosses, hybrid production, crosses to populations, and the like. All plants produced using inbred corn line PHP60 as a parent are within the scope of this invention. Advantageously, the inbred corn line is used in crosses with other, different, corn inbreds to produce first generation ($F_1$) corn hybrid seeds and plants with superior characteristics.

As used herein, the terms "plant and plant parts" include plant cells, plant protoplasts, plant cell tissue culture from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like.

Tissue culture of corn is described in European Patent Application, publication 160,390, incorporated herein by reference. Corn tissue culture procedures are also described in Green and Rhodes, "Plant Regeneration in Tissue Culture of Maize," *Maize for Biological Research* (Plant Molecular Biology Association, Charlottsville, Va. 1982, at 367–372. Thus, another aspect of this invention is to provide cells which upon growth and differentiation produce the inbred line PHP60.

The utility of inbred line PHP60 also extends to crosses with other species. Commonly, suitable species will be of the family Graminaceae, and especially of the genera Zea, Tripsacum, Coix, Schlerachne, Polytoca, Chionachne, and Trilobachne, of the tribe Maydeae. Of these, Zea and Tripsacum, are most preferred. Potentially suitable for crosses with PHP60 may be the various varieties of grain sorghum, *Sorghum bicolor* (L.) Moench.

Corn is used as human food, livestock feed, and as raw material in industry. The food uses of corn, in addition to human consumption of corn kernels, include both products of dry- and wet-milling industries and alkaline cooking. The principal products of corn dry milling are grits, meal and flour. The corn wet-milling industry can provide corn starch, corn syrups, and dextrose for food use. Alkaline cooking provides snack foods (i.e., corn chips, tortillas, etc.) Corn oil is recovered from corn germ, which is a by-product of both dry- and wet-milling industries.

Corn, including both grain and non-grain portions of the plant, is also used extensively as livestock feed, primarily for beef cattle, dairy cattle, hogs, and poultry.

Industrial uses of corn are mainly from corn starch from the wet-milling industry and corn flour from the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel and to make charcoal.

The seed of inbred corn line PHP60, the plant produced from the inbred seed, the hybrid corn plant produced from the crossing of the inbred, hybrid seed, and various parts of the hybrid corn plant can be utilized for human food, livestock feed, and as a raw material in industry

EXAMPLE

Inbred and Hybrid performance of PHP60

In the examples that follow the traits and characteristics of inbred corn line PHP60 are given as a line and in hybrid combination. The data collected on inbred corn line PHP60 is presented for the key characteristics and traits.

The results in Table 3 compare PHP60 to B73. B73 is an important inbred developed by Iowa State University and is used in the area that PHP60 would be used and would cross well with some of the same inbred lines. The results show that the two inbreds differ significantly for a number of traits. PHP60 is later maturing (flowering and harvest moisture of grain), has higher percentage of large kernels, is shorter and lower eared, has harder textured grain, higher stay green scores, and better stalk lodging resistance than B73. PHP60 has better ear mold tolerance, gray leaf spot tolerance, and much better southern leaf blight tolerance which makes it an important new female to use in the South.

The results in Table 4 compare PHP60 to PHV78. PHV78 (PVP Certificate #8800003, U.S. Pat. No. 4,812,599) is an important inbred that would be used in the area that PHP60 would be used and would cross well with some of the same inbred lines. This data was collected over four years of research testing. The results show that the two inbreds differ significantly for a number of traits. PHP60 had a five-bushel per acre yield advantage over PHV78, had higher grain test weight with better grain quality and harder textured grain, and better stay green than PHV78. PHP60 was also more resistant to southern leaf blight, gray leaf spot, fusarium and general ear molds than PHV78.

The results in Table 5A compare a PHP60 hybrid to a B73 hybrid from one research station in the south central Corn Belt. Although the data is limited it shows some significant differences between the B73 and PHP60 hybrids. The PHP60 hybrid was later maturing (flowering and grain harvest moisture) and had better stay green.

The results in Table 5B compare PHP60 to PHV78 crossed to the same inbred testers. This data was collected in the Central and Southern Corn Belt. The results show that the two lines also differ significantly for a number of traits in hybrid combination. The PHP60 hybrids had better resistance to root lodging, better stay green and better grain test weight than the PHV78 hybrids. PHP60 has given good performance in specific hybrid combinations for the Southeast.

The results in Table 6 compare a PHP60 hybrid to Pioneer ® Brand hybrid 3343 where both hybrids have a parent in common (not PHP60). This data has been collected over one year of research testing in the central and southern Corn Belt. The data in the comparison is from Shelbyville, Illinois and Union City, Tennessee. The comparison shows that the PHP60 hybrid has much higher test weight grain than 3343.

The results in Table 7 compare the performance of a PHP60 hybrid to Pioneer ® Brand 3295 where the hybrids have a parent in common (not PHP60). The hybrid 3295 is grown in some of the areas where the PHP60 hybrid is grown but will not be utilized as far south. The PHP60 hybrid is later for harvest moisture maturity, has higher yields, better stay green, improved test weight, better grain quality and is a taller hybrid than 3295.

The results in Table 8 compare the performance of a PHP60 hybrid to Pioneer ® Brand 3140. Although the two hybrids have no parents in common, 3140 is a fairly new very important hybrid that is used in the same area as the PHP60 hybrid. The PHP60 hybrid has higher yield, lower harvest moisture of the grain, with better test weight and grain quality, and improved stand establishment in the spring compared to 3140. These characteristics will make the PHP60 hybrid very important in the Southeast.

TABLE 3

PAIRED INBRED COMPARISON DATA
INBRED #1 — PHP 60
INBRED #2 — B73

\* = 10% SIG  + = 5% SIG  # = 1% SIG

| YEAR | VAR # | BU ACR ABS | BU ACR % MN | BAR PLT ABS | BRT STK ABS | EAR HT ABS | EAR SZ ABS | EST CNT ABS | CLD TST ABS | CLD TST % MN | DRP EAR ABS | TIL LER ABS | GDU SHD ABS | GDU SLK ABS |
|---|---|---|---|---|---|---|---|---|---|---|---|---|---|---|
| TOTAL SUM | 1 | 66.2 | 93 | 81.4 | 87.9 | 27.7 | 6.2 | 37.1 | 66.7 | 81 | 100.0 | 14.8 | 163.2 | 167.7 |
|  | 2 | 77.8 | 116 | 92.6 | 83.8 | 32.0 | 5.9 | 41.4 | 78.9 | 100 | 99.8 | 0.5 | 154.3 | 158.3 |
|  | LOCS | 43 | 43 | 33 | 4 | 34 | 18 | 98 | 12 | 12 | 4 | 23 | 78 | 70 |
|  | DIFF | 11.6 | 23 | 11.2 | 4.1 | 4.3 | 0.4 | 4.3 | 12.3 | 19 | 0.2 | 14.3 | 8.9 | 9.5 |
|  | PROB | .027+ | .015+ | .001# | .618 | .000# | .313 | .000# | .058* | .072* | .391 | .035+ | .000# | .000# |

| YEAR | VAR # | GRN QUL ABS | KER LB ABS | KSZ XL ABS | KSZ L ABS | KSZ MR ABS | KSZ MF ABS | KSZ S ABS | KSZ TIP ABS | MST ABS | PLT HT ABS | POL SC ABS | RT LDG ABS |
|---|---|---|---|---|---|---|---|---|---|---|---|---|---|
| TOTAL SUM | 1 | 6.2 | 173.8 | 0.4 | 26.0 | 54.0 | 12.6 | 6.6 | 0.6 | 20.1 | 75.0 | 4.9 | 79.3 |
|  | 2 | 6.1 | 214.9 | 0.0 | 1.2 | 14.8 | 21.2 | 45.4 | 17.6 | 18.3 | 79.4 | 5.5 | 88.3 |
|  | LOCS | 15 | 12 | 5 | 5 | 5 | 5 | 5 | 5 | 44 | 36 | 22 | 19 |
|  | DIFF | 0.1 | 41.1 | 0.4 | 24.8 | 39.2 | 8.6 | 38.8 | 17.0 | 1.8 | 4.4 | 0.5 | 9.0 |
|  | PROB | .848 | .007# | .178 | .100 | .004# | .392 | .004# | .053* | .000# | .007# | .074* | .043+ |

| YEAR | VAR # | TAS BLS ABS | TAS SZ ABS | TEX EAR ABS | TST WT ABS | SCT GRN ABS | SDG VGR ABS | STA GRN ABS | STK CNT ABS | STK LDG ABS | YLD SC ABS | COM RST ABS | COM SMT ABS | EAR MLD ABS |
|---|---|---|---|---|---|---|---|---|---|---|---|---|---|---|
| TOTAL SUM | 1 | 9.0 | 4.3 | 7.5 | 57.5 | 5.5 | 3.9 | 6.4 | 32.8 | 95.3 | 5.4 | 4.0 | 0.0 | 6.8 |
|  | 2 | 1.0 | 5.2 | 5.8 | 57.8 | 7.4 | 6.1 | 2.3 | 34.0 | 86.0 | 6.8 | 6.3 | 7.0 | 6.2 |
|  | LOCS | 1 | 33 | 13 | 43 | 25 | 51 | 53 | 99 | 16 | 28 | 3 | 1 | 28 |
|  | DIFF | 8.0 | 0.8 | 1.7 | 0.3 | 1.8 | 2.1 | 4.1 | 1.1 | 9.3 | 1.4 | 2.3 | 7.0 | 0.6 |
|  | PROB |  | .000# | .001# | .244 | .003# | .000# | .000# | .001# | .043+ | .009# | .192 |  | .065* |

| YEAR | VAR # | ECB DPE ABS | ECB 1LF ABS | ECB 2SC ABS | EYE SPT ABS | FUS EAR ABS | GLF SPT ABS | MDM CPX ABS | NLF BLT ABS | SLF BLT ABS | SO RST ABS | STW WLT ABS |
|---|---|---|---|---|---|---|---|---|---|---|---|---|
| TOTAL SUM | 1 | 86.7 | 3.7 | 5.0 | 7.0 | 50.9 | 4.2 | 3.2 | 3.8 | 6.8 | 5.0 | 7.5 |
|  | 2 | 53.3 | 3.6 | 3.3 | 5.0 | 76.1 | 2.3 | 2.0 | 3.3 | 3.2 | 5.5 | 7.0 |
|  | LOCS | 1 | 11 | 3 | 1 | 4 | 8 | 3 | 3 | 12 | 1 | 2 |
|  | DIFF | 33.3 | 0.1 | 1.7 | 2.0 | 25.1 | 1.9 | 1.2 | 0.5 | 3.5 | 0.5 | 0.5 |
|  | PROB |  | .779 | .300 |  | .103 | .001# | .118 | .762 | .000# |  | .500 |

TABLE 4

PAIRED INBRED COMPARISON DATA
INBRED #1 — PHP60
INBRED #2 — PHV78

\* = 10% SIG  + = 5% SIG  # = 1% SIG

| YEAR | VAR # | BU ACR ABS | BU ACR % MN | BAR PLT ABS | BRT STK ABS | EAR HT ABS | EAR SZ ABS | EST CNT ABS | TIL LER ABS | GDU SHD ABS | GDU SLK ABS | GRN QUL ABS | MST ABS | PLT HT ABS |
|---|---|---|---|---|---|---|---|---|---|---|---|---|---|---|
| TOTAL SUM | 1 | 88.8 | 126 | 79.0 | 95.2 | 29.7 | 6.0 | 30.6 | 12.7 | 163.7 | 167.3 | 8.3 | 21.5 | 81.6 |
|  | 2 | 83.0 | 117 | 96.1 | 92.1 | 29.2 | 7.0 | 29.4 | 2.0 | 158.6 | 164.7 | 5.8 | 16.2 | 83.4 |
|  | LOCS | 16 | 16 | 14 | 3 | 22 | 21 | 71 | 19 | 66 | 64 | 6 | 16 | 23 |
|  | DIFF | 5.8 | 9 | 17.1 | 3.1 | 0.5 | 1.0 | 1.2 | 10.6 | 5.1 | 2.6 | 2.4 | 5.3 | 1.8 |
|  | PROB | .173 | .150 | .074* | .326 | .574 | .002# | .095* | .071* | .000# | .032+ | .042+ | .000# | .418 |

| YEAR | VAR # | POL WT ABS | POL WT % MN | POL SC ABS | RT LDG ABS | TAS SZ ABS | TAS WT ABS | TEX EAR ABS | TST WT ABS | SCT GRN ABS | SDG VGR ABS | STA GRN ABS | STK CNT ABS | STK LDG ABS |
|---|---|---|---|---|---|---|---|---|---|---|---|---|---|---|

TABLE 4-continued

PAIRED INBRED COMPARISON DATA
INBRED #1 — PHP60
INBRED #2 — PHV78

\* = 10% SIG + = 5% SIG # = 1% SIG

| | | | | | | | | | | | | | | |
|---|---|---|---|---|---|---|---|---|---|---|---|---|---|---|
| TOTAL SUM | 1 | 83.3 | 42 | 5.0 | 71.2 | 4.3 | 2.8 | 7.5 | 57.6 | 5.4 | 4.1 | 6.5 | 27.0 | 93.5 |
| | 2 | 259.7 | 140 | 7.0 | 82.1 | 6.9 | 5.8 | 4.2 | 55.2 | 5.8 | 5.2 | 5.1 | 25.7 | 97.8 |
| | LOCS | 3 | 3 | 26 | 7 | 33 | 3 | 15 | 16 | 26 | 36 | 34 | 68 | 3 |
| | DIFF | 176.4 | 98 | 2.0 | 11.0 | 2.6 | 3.0 | 3.3 | 2.4 | 0.3 | 1.2 | 1.4 | 1.4 | 4.3 |
| | PROB | .057\* | .082\* | .000# | .424 | .000# | .008# | .000# | .001# | .486 | .000# | .000# | .008# | .481 |

| YEAR | VAR # | YLD SC ABS | ANT ROT ABS | CLN ABS | COM RST ABS | COM SMT ABS | EAR MLD ABS | ECB DPE ABS | ECB 1LF ABS | ECB 2SC ABS | ECB 2IT ABS | EYE SPT ABS | FUS EAR ABS | GLF SPT ABS |
|---|---|---|---|---|---|---|---|---|---|---|---|---|---|---|
| TOTAL SUM | 1 | 5.0 | 5.5 | 2.0 | 4.0 | 0.0 | 6.7 | 91.7 | 4.1 | .5.5 | 5.9 | 7.0 | 56.8 | 4.3 |
| | 2 | 6.0 | 5.5 | 5.5 | 4.3 | 0.0 | 5.0 | 85.0 | 5.7 | 4.5 | 9.2 | 3.0 | 39.8 | 2.9 |
| | LOCS | 30 | 1 | 1 | 3 | 1 | 29 | 2 | 16 | 6 | 1 | 1 | 7 | 12 |
| | DIFF | 1.0 | 0.0 | 3.5 | 0.3 | 0.0 | 1.8 | 6.7 | 1.7 | 1.0 | 3.3 | 4.0 | 17.0 | 1.3 |
| | PROB | .038+ | | | .874 | | .000# | .500 | .001# | .159 | | | .083\* | .000# |

| YEAR | VAR # | HC BLT ABS | HD SMT ABS | MDM CPX ABS | NLF BLT ABS | SLF BLT ABS | SO RST ABS | STW WLT ABS |
|---|---|---|---|---|---|---|---|---|
| TOTAL SUM | 1 | 5.5 | 100.0 | 3.3 | 3.8 | 6.6 | 5.0 | 5.9 |
| | 2 | 5.0 | 98.8 | 2.8 | 5.7 | 5.0 | 6.0 | 6.8 |
| | LOCS | 1 | 2 | 4 | 6 | 12 | 1 | 4 |
| | DIFF | 0.5 | 1.2 | 0.5 | 1.8 | 1.5 | 1.0 | 0.9 |
| | PROB | | .500 | .391 | .048+ | .006# | | .310 |

TABLES 5A & 5B

Average Inbred by Tester Performance Comparing PHP60 to B73 and PHP60 TO PHV78 crossed to the same Inbred Tester(s) and Grown in the Same Experiments. All Values are Expressed as percent of the experiment mean except Predicted RM, Selection Index, and Yield (Bu./Ac.).

PHP60 to B73

| | Inbred | PRM | SEL IND | BU ACR | YLD | MST | GDU SHD | STK LDG | RT LDG | BAR PLT | STA GRN |
|---|---|---|---|---|---|---|---|---|---|---|---|
| TOTAL | REPLIC. | 6 | 6 | 6 | 6 | 6 | 4 | 8 | 4 | 6 | 6 |
| MEAN WTS | B73 | 125 | 111 | 180 | 112 | 97 | 100 | 94 | 82 | 102 | 100 |
| MEAN WTS | PHP60 | 130 | 98 | 171 | 101 | 107 | 107 | 99 | 76 | 96 | 138 |
| | DIFF. | 5 | 14 | 9 | 11 | 10 | 7 | 5 | 6 | 6 | 38 |

| | Inbred | TST WTA | COB SC | GRN QUL | SDG VGR | EST CNT | PLT HT | EAR HT | DRP EAR | BRT STK |
|---|---|---|---|---|---|---|---|---|---|---|
| TOTAL | REPLIC. | 6 | | | 4 | 4 | 6 | 6 | | |
| MEAN WTS | B73 | 102 | | | 80 | 105 | 106 | 112 | | |
| MEAN WTS | PHP60 | 102 | | | 53 | 92 | 107 | 105 | | |
| | DIFF. | 0 | | | 26 | 13 | 1 | 7 | | |

PHP60 to PHV78

| | Inbred | PRM | SEL IND | BU ACR | YLD | MST | GDU SHD | STK LDG | RT LDG | BAR PLT | STA GRN |
|---|---|---|---|---|---|---|---|---|---|---|---|
| TOTAL | REPLIC. | 26 | 26 | 26 | 26 | 26 | 6 | 12 | 20 | 2 | 22 |
| MEAN WTS | PHP60 | 125 | 95 | 147 | 95 | 97 | 101 | 87 | 101 | 100 | 103 |
| MEAN WTS | PHV78 | 123 | 102 | 158 | 104 | 95 | 100 | 86 | 94 | 102 | 83 |
| | DIFF. | 2 | 7 | 11 | 8 | 2 | 0 | 1 | 7 | 2 | 20 |

| | Inbred | TST WTA | COB SC | GRN QUL | SDG VGR | EST CNT | PLT HT | EAR HT | DRP EAR | BRT STK |
|---|---|---|---|---|---|---|---|---|---|---|
| TOTAL | REPLIC. | 26 | 4 | 6 | 16 | 24 | 12 | 16 | | |
| MEAN WTS | PHP60 | 103 | 98 | 96 | 91 | 95 | 100 | 98 | | |
| MEAN WTS | PHV78 | 98 | 92 | 100 | 96 | 102 | 100 | 101 | | |
| | DIFF. | 5 | 6 | 4 | 5 | 7 | 0 | 2 | | |

TABLE 6

1 — PHP60 HYBRID
2 — PIONEER ® BRAND 3343

\* = 10% SIG + = 5% SIG # = 1% SIG

| YEAR | VAR # | SEL IND | PRM | BU ACR ABS | MST ABS | GDU SHD ABS | STK LDG ABS | RT LDG ABS | STA GRN ABS |
|---|---|---|---|---|---|---|---|---|---|
| TOTAL SUM | 1 | 94 | 123 | 136.1 | 20.2 | 138.0 | 100.0 | 99.4 | 5.6 |
| | 2 | 109 | 122 | 154.5 | 18.7 | 136.0 | 97.1 | 94.9 | 4.2 |
| | LOCS | 2 | 1 | 6 | 6 | 1 | 3 | 4 | 5 |
| | DIFF | 15 | 1 | 18.4 | 1.5 | 2.0 | 2.9 | 4.4 | 1.4 |

TABLE 6-continued

1 — PHP60 HYBRID
2 — PIONEER ® BRAND 3343

\* = 10% SIG   + = 5% SIG   # = 1% SIG

| | | PROB | .065* | | .068* | .160 | | .193 | .140 | .296 |

| YEAR | VAR # | TST WTA ABS | COB SC ABS | GRN QUL ABS | SDG VGR ABS | EST CNT ABS | PLT HT ABS | EAR HT ABS |
|---|---|---|---|---|---|---|---|---|
| TOTAL SUM | 1 | 59.3 | 6.5 | 8.7 | 4.5 | 44.6 | 101.2 | 39.3 |
| | 2 | 56.7 | 5.5 | 8.2 | 7.2 | 53.9 | 101.3 | 42.6 |
| | LOCS | 6 | 1 | 3 | 3 | 5 | 3 | 4 |
| | DIFF | 2.6 | 1.0 | 0.5 | 2.7 | 9.3 | 0.2 | 3.4 |
| | PROB | .006# | | .225 | .202 | .003# | .840 | .278 |

TABLE 7

1 — PHP60 HYBRID
2 — PIONEER ® BRAND 3295

\* = 10% SIG   + = 5% SIG   # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS | TST WTA ABS |
|---|---|---|---|---|---|---|---|---|---|---|---|---|---|
| TOTAL SUM | | 1 | 127 | 110 | 159.4 | 111 | 20.5 | 148.5 | 92.2 | 80.2 | 96.5 | 5.4 | 56.8 |
| | | 2 | 125 | 107 | 152.1 | 105 | 19.4 | 144.0 | 94.8 | 91.4 | 97.2 | 4.8 | 56.6 |
| | | LOCS | 43 | 43 | 166 | 166 | 166 | 39 | 109 | 69 | 28 | 117 | 160 |
| | | DIFF | 3 | 3 | 7.3 | 6 | 1.1 | 4.5 | 2.7 | 11.3 | 0.6 | 0.6 | 0.2 |
| | | PROB | .000# | .111 | .000# | .000# | .000# | .000# | .012+ | .000# | .293 | .000# | .011+ |

| YEAR | REGION | VAR # | COB SC ABS | GRN QUL ABS | SDG VGR ABS | EST CNT ABS | STK CNT ABS | PLT HT ABS | EAR HT ABS | DRP EAR ABS | BRT STK ABS |
|---|---|---|---|---|---|---|---|---|---|---|---|
| TOTAL SUM | | 1 | 4.6 | 6.1 | 5.2 | 54.6 | 43.1 | 115.6 | 50.3 | 99.7 | 98.6 |
| | | 2 | 5.6 | 5.6 | 7.0 | 56.3 | 43.2 | 113.5 | 49.0 | 99.7 | 100.0 |
| | | LOCS | 14 | 91 | 79 | 109 | 171 | 95 | 102 | 20 | 1 |
| | | DIFF | 1.1 | 0.5 | 1.8 | 1.8 | 0.1 | 2.1 | 1.3 | 0.0 | 1.4 |
| | | PROB | .002# | .000# | .000# | .000# | .357 | .000# | .000# | .944 | |

TABLE 8

1 — PHP60 HYBRID
2 — PIONEER ® BRAND 3140

\* = 10% SIG   + = 5% SIG   # = 1% SIG

| YEAR | REGION | VAR # | PRM | SEL IND | BU ACR ABS | BU ACR % MN | MST ABS | GDU SHD ABS | STK LDG ABS | RT LDG ABS | BAR PLT ABS | STA GRN ABS | TST WTA ABS |
|---|---|---|---|---|---|---|---|---|---|---|---|---|---|
| TOTAL SUM | | 1 | 127 | 109 | 154.0 | 110 | 19.8 | 149.5 | 89.6 | 79.7 | 97.5 | 5.0 | 57.1 |
| | | 2 | 128 | 108 | 148.4 | 106 | 20.2 | 149.4 | 94.6 | 89.2 | 98.2 | 5.5 | 56.6 |
| | | LOCS | 31 | 30 | 121 | 121 | 123 | 23 | 77 | 38 | 12 | 82 | 114 |
| | | DIFF | 1 | 1 | 5.6 | 4 | 0.3 | 0.1 | 4.9 | 9.5 | 0.6 | 0.5 | 0.5 |
| | | PROB | .001# | .604 | .001# | .001# | .003# | .891 | .000# | .002# | .447 | .004# | .000# |

| YEAR | REGION | VAR # | COB SC ABS | GRN QUL ABS | SDG VGR ABS | EST CNT ABS | STK CNT ABS | PLT HT ABS | EAR HT ABS | DRP EAR ABS | BRT STK ABS |
|---|---|---|---|---|---|---|---|---|---|---|---|
| TOTAL SUM | | 1 | 4.9 | 6.0 | 5.1 | 55.1 | 43.9 | 116.3 | 50.8 | 99.7 | 98.6 |
| | | 2 | 5.3 | 5.7 | 5.0 | 53.0 | 43.4 | 115.2 | 51.2 | 99.7 | 96.7 |
| | | LOCS | 8 | 81 | 61 | 67 | 124 | 63 | 66 | 12 | 1 |
| | | DIFF | 0.3 | 0.3 | 0.1 | 2.1 | 0.5 | 1.2 | 0.4 | 0.0 | 1.9 |
| | | PROB | .279 | .024+ | .279 | .004# | .044+ | .042+ | .350 | .918 | |

Applicants have made available to the public without restriction a deposit of at least 2500 seeds of inbred PHP60 with the American Type Culture Collection (ATCC), Rockville, MD 20852 USA, ATCC Deposit No. 75078. The seeds deposited with the ATCC are taken from the same deposit maintained by Pioneer Hi-Bred International Inc., 700 Capital Square, 400 Locust St., Des Moines, Iowa 50309 since prior to the filing date of this application. The deposit will be maintained in the ATCC depository, which is a public depository, for a period of 30 years, or 5 years after the most recent request, or for the effective life of the patent, whichever is longer, and will be replaced if it becomes nonviable during that period.

What is claimed is:

1. Inbred corn seed designated PHP60 having ATCC accession No.
2. A corn plant produced by the seed of claim 1.
3. Tissue culture of the plant of claim 2.
4. Tissue culture according to claim 3 comprising regenerable cells of a plant part selected from meristematic tissue, anthers, leaves, embryos, protoplasts, and pollen.
5. A corn plant regenerated from the regenerable cells of a tissue culture according to claim 4.
6. An inbred corn plant having all the physiological and morphological characteristics of the seed of claim 1.

* * * * *